United States Patent
Govari

(10) Patent No.: US 10,820,923 B2
(45) Date of Patent: Nov. 3, 2020

(54) INSERTION TUBE WITH DEFLECTABLE TIP

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 588 days.

(21) Appl. No.: 15/155,850

(22) Filed: May 16, 2016

(65) Prior Publication Data

US 2017/0325841 A1 Nov. 16, 2017

(51) Int. Cl.
*A61B 17/34* (2006.01)
*A61B 1/005* (2006.01)
*A61B 1/233* (2006.01)

(52) U.S. Cl.
CPC ........ *A61B 17/3417* (2013.01); *A61B 1/0052* (2013.01); *A61B 1/0055* (2013.01); *A61B 1/0057* (2013.01); *A61B 1/0058* (2013.01); *A61B 1/233* (2013.01); *A61B 2017/345* (2013.01)

(58) Field of Classification Search
CPC ... A61B 17/3417; A61B 1/005; A61B 1/0051; A61B 1/0057
See application file for complete search history.

(56) References Cited

U.S. PATENT DOCUMENTS

| 3,664,330 A | * | 5/1972 | Deutsch | A61B 1/00165 385/902 |
| 4,737,141 A | * | 4/1988 | Spits | A61M 25/04 604/106 |
| 5,179,934 A | * | 1/1993 | Nagayoshi | A61B 1/00183 600/152 |
| 5,448,989 A | * | 9/1995 | Heckele | A61B 1/0055 600/104 |
| 5,472,017 A | * | 12/1995 | Kovalcheck | A61B 1/0052 138/103 |
| 5,549,637 A | * | 8/1996 | Crainich | A61B 17/29 606/170 |

(Continued)

FOREIGN PATENT DOCUMENTS

| AU | 2012244072 A1 | 11/2012 |
| WO | WO 1994/010897 A1 | 5/1994 |
| WO | WO 2016/035084 A2 | 3/2016 |

OTHER PUBLICATIONS

Partial European Search Report dated Oct. 24, 2017 for Application No. 17171323.3, 10 pages.

(Continued)

*Primary Examiner* — Julie A Szpira
(74) *Attorney, Agent, or Firm* — Frost Brown Todd LLC

(57) ABSTRACT

Apparatus described herein includes a tube, shaped to define a tube lumen and including a distal portion that has a plurality of articulated sections. The apparatus further includes a ribbon that passes longitudinally through the tube lumen and is connected to a distalmost one of the articulated sections, and a control handle disposed at a proximal end of the tube, the control handle being configured to flex the distal portion of the tube by pulling the ribbon. Other embodiments are also described.

20 Claims, 3 Drawing Sheets

(56) References Cited

U.S. PATENT DOCUMENTS

| | | | | |
|---|---|---|---|---|
| 5,766,196 A * | 6/1998 | Griffiths | A61B 17/29 | 600/564 |
| 6,053,172 A * | 4/2000 | Hovda | A61B 18/1402 | 128/898 |
| 6,270,453 B1 * | 8/2001 | Sakai | A61B 1/0055 | 600/141 |
| 6,306,084 B1 * | 10/2001 | Pinczower | A61B 1/233 | 600/184 |
| 6,569,105 B1 * | 5/2003 | Kortenbach | A61B 10/06 | 600/562 |
| 6,641,528 B2 * | 11/2003 | Torii | A61B 1/0052 | 600/142 |
| 6,743,239 B1 * | 6/2004 | Kuehn | A61B 17/0643 | 464/149 |
| 6,817,974 B2 * | 11/2004 | Cooper | A61B 17/00234 | 600/142 |
| 6,911,039 B2 * | 6/2005 | Shiu | A61F 2/95 | 623/1.12 |
| 7,371,210 B2 * | 5/2008 | Brock | A61B 17/0469 | 600/114 |
| 8,568,439 B2 * | 10/2013 | Keith | A61B 17/12022 | 606/196 |
| 8,795,306 B2 * | 8/2014 | Smith | A61B 17/32075 | 606/159 |
| 8,951,225 B2 * | 2/2015 | Evard | A61M 25/10 | 604/96.01 |
| 9,005,114 B2 * | 4/2015 | Zubiate | A61B 1/0053 | 600/170 |
| 9,211,134 B2 * | 12/2015 | Stroup | A61B 17/29 | |
| 9,220,559 B2 * | 12/2015 | Worrell | A61B 18/1445 | |
| 10,029,073 B2 * | 7/2018 | Kabe | A61M 25/0138 | |
| 10,052,457 B2 * | 8/2018 | Nguyen | A61M 25/0043 | |
| 10,188,413 B1 * | 1/2019 | Morriss | A61B 17/24 | |
| 10,265,056 B2 * | 4/2019 | Stanton | A61B 17/00234 | |
| 2002/0087049 A1 * | 7/2002 | Brock | A61B 17/0469 | 600/114 |
| 2003/0083550 A1 * | 5/2003 | Miyagi | A61B 1/0055 | 600/141 |
| 2005/0107667 A1 * | 5/2005 | Danitz | A61B 1/0053 | 600/139 |
| 2006/0095066 A1 * | 5/2006 | Chang | A61B 17/1204 | 606/199 |
| 2006/0111615 A1 * | 5/2006 | Danitz | A61B 1/00071 | 600/141 |
| 2008/0015544 A1 * | 1/2008 | Keith | A61B 17/12022 | 604/516 |
| 2008/0188868 A1 * | 8/2008 | Weitzner | A61B 1/0014 | 606/130 |
| 2008/0287741 A1 * | 11/2008 | Ostrovsky | A61B 1/00071 | 600/141 |
| 2011/0264136 A1 * | 10/2011 | Choi | A61B 34/71 | 606/205 |
| 2012/0136207 A1 | 5/2012 | Goldfarb et al. | | |
| 2012/0190924 A1 * | 7/2012 | Tseng | A61B 1/00066 | 600/127 |
| 2012/0265094 A1 * | 10/2012 | Goldfarb | A61B 1/0014 | 600/562 |
| 2013/0253387 A1 | 9/2013 | Bonutti et al. | | |
| 2013/0253481 A1 * | 9/2013 | Dewaele | A61B 1/00071 | 606/1 |
| 2013/0267936 A1 * | 10/2013 | Stroup | A61B 17/29 | 606/1 |
| 2014/0012276 A1 | 1/2014 | Alvarez | | |
| 2014/0135685 A1 * | 5/2014 | Kabe | A61M 25/0138 | 604/95.04 |
| 2014/0330432 A1 * | 11/2014 | Simaan | B25J 9/1633 | 700/250 |
| 2017/0071687 A1 * | 3/2017 | Cohen | A61B 90/50 | |
| 2017/0231701 A1 * | 8/2017 | Cohen | A61B 90/50 | 600/104 |

OTHER PUBLICATIONS

European Search Report dated Feb. 26, 2018 for Application No. 17171323.3, 9 pages.

* cited by examiner

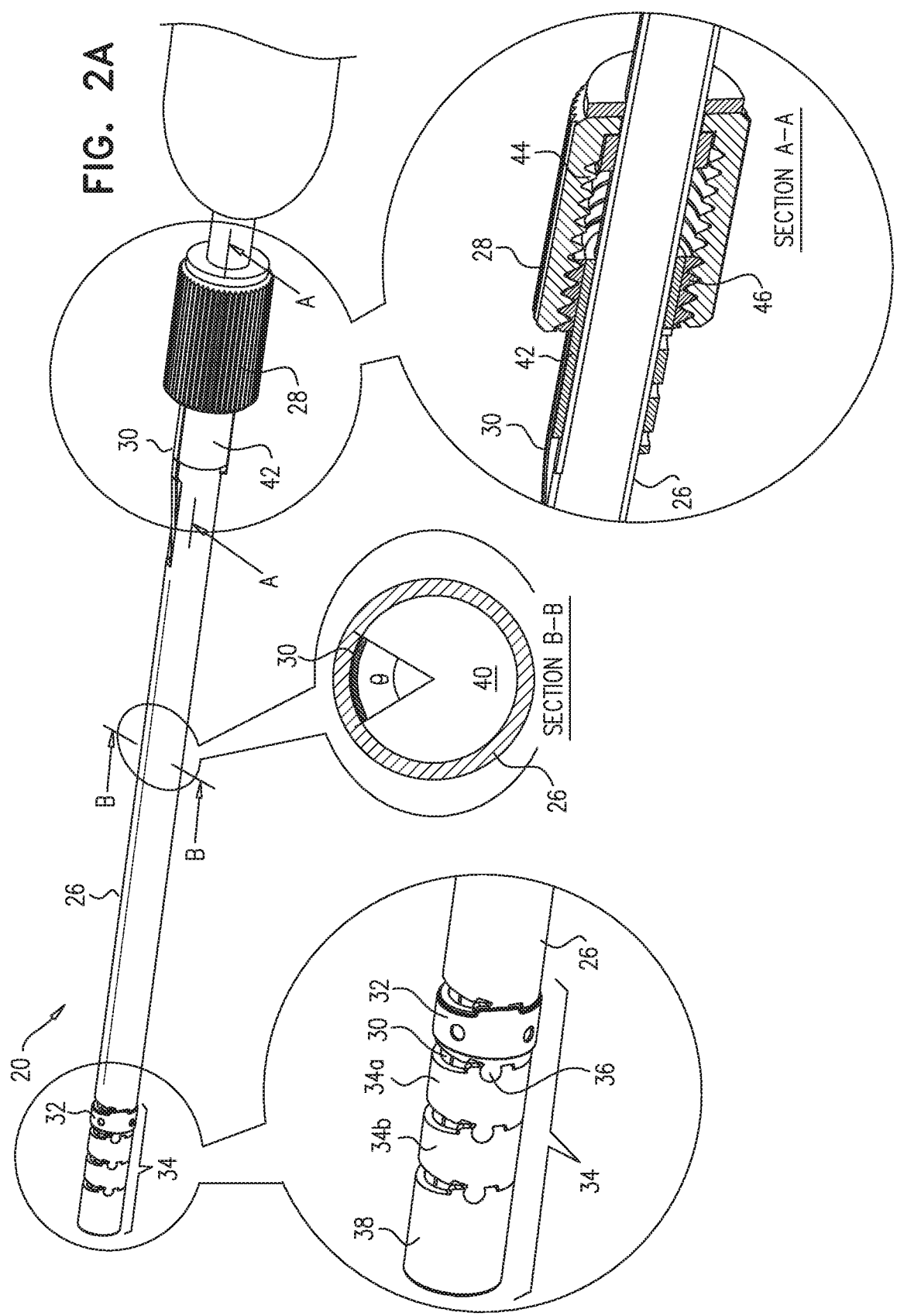

INSERTION TUBE WITH DEFLECTABLE TIP

FIELD OF THE INVENTION

Embodiments of the present invention relate generally to the field of medical procedures, and specifically to apparatus and methods for facilitating the insertion of a tool into an interior portion of a body of a subject, such as the sinus of the subject.

BACKGROUND

In some cases, it is necessary to insert a camera, balloon catheter, or other tool into a sinus of a subject, to facilitate treatment of the sinus.

US Patent Publication 2012/0265094, issued as U.S. Pat. No. 9,468,362 on Oct. 18, 2016, whose disclosure is incorporated herein by reference, describes medical devices, systems and methods that are useable to facilitate transnasal insertion and positioning of guidewires and various other devices and instruments at desired locations within the ear, nose, throat, paranasal sinuses or cranium, and the direct viewing of such placements via an endoscope.

Australian Patent Application No. 2012244072, whose disclosure is incorporated herein by reference, describes methods and apparatus for treating disorders of the ear, nose, throat or paranasal sinuses, including methods and apparatus for dilating ostia, passageways and other anatomical structures, endoscopic methods and apparatus for endoscopic visualization of structures within the ear, nose, throat or paranasal sinuses, navigation devices for use in conjunction with image guidance or navigation system and hand held devices having pistol type grips and other handpieces.

US Patent Publication 2014/0012276, issued as U.S. Pat. No. 9,504,604 on Nov. 29, 2016, whose disclosure is incorporated herein by reference, describes a lithotripsy probe used to break up cataracts, sinus blockages and other body masses, where the broken materials may be removed by suction. The lithotripsy probe may have a spark generator, a fluid motion generator, or other component for breaking up the body mass.

US Patent Publication 2013/0253387, now abandoned, whose disclosure is incorporated herein by reference, describes systems and methods for treating an occluded area in a body, accessing cavities or passages of the body, or reducing pathologic material in the body. Embodiments may be configured to apply vibratory energy to pathologic material in a treatment area of a body. A handle connected to an energy source may be configured to provide an energy signal. A transducer may be configured to receive the energy signal. An effector may be operatively coupled to the transducer. The effector may have a proximal end connected to the handle and a distal portion configured to apply vibratory energy to pathologic material. A cannula may have a longitudinal passage to receive at least a portion of the effector and/or be configured to expose at least the distal portion of the effector to the pathologic material or the treatment area.

US Patent Publication 2012/0136207, issued as U.S. Pat. No. 9,107,574 on Aug. 18, 2015, whose disclosure is incorporated herein by reference, describes medical devices, systems and methods that are useable to facilitate transnasal insertion and positioning of guidewires and various other devices and instruments at desired locations within the ear, nose, throat, paranasal sinuses or cranium.

SUMMARY OF THE INVENTION

There is provided, in accordance with some embodiments of the present invention, apparatus that includes a tube, shaped to define a tube lumen and including a distal portion that includes a plurality of articulated sections. The apparatus further includes a ribbon that passes longitudinally through the tube lumen and is connected to a distalmost one of the articulated sections, and a control handle disposed at a proximal end of the tube. The control handle is configured to flex the distal portion of the tube by pulling the ribbon.

In some embodiments, the ribbon includes nitinol.

In some embodiments, the control handle includes a turnable dial configured to (i) by turning in a first direction, pull the ribbon, and (ii) by turning in a second direction that is opposite the first direction, push the ribbon.

In some embodiments, the turnable dial is further configured to, subsequently to turning, hold the ribbon in place.

In some embodiments, at least one pair of the articulated sections includes:

a first articulated section, shaped to define two grooves; and a second articulated section, including two protrusions configured to swivelingly fit within the grooves such that one of the first articulated section and the second articulated section swivels with respect to the other one of the first articulated section and the second articulated section, as the ribbon is pulled.

In some embodiments, the ribbon has a curved cross-section.

In some embodiments, an angle between two hypothetical lines that are tangent to respective ends of the cross-section of the ribbon is between 50 and 70 degrees.

In some embodiments, the articulated sections consist of between 3 and 10 articulated sections.

In some embodiments, the ribbon is at a distal end of a control tube that runs longitudinally within the tube lumen proximally to the distal portion of the tube, the control handle being configured to pull the ribbon by pulling the control tube.

In some embodiments, the apparatus further includes casing elements that cover the articulated sections.

There is further provided, in accordance with some embodiments of the present invention, a method that includes, by pulling a ribbon, flexing a distal portion of a tube, and subsequently, while the distal portion of the tube is flexed, passing a tool longitudinally through a lumen of the tube and into an interior portion of a body of a subject.

In some embodiments, the interior portion of the body of the subject includes a sinus of the subject.

The present invention will be more fully understood from the following detailed description of embodiments thereof, taken together with the drawings, in which:

BRIEF DESCRIPTION OF THE DRAWINGS

FIGS. 1 and 2A-B are schematic illustrations of apparatus for facilitating insertion of a tool into a sinus of a subject, in accordance with some embodiments of the present invention.

DETAILED DESCRIPTION OF EMBODIMENTS

Overview

Due to the anatomy of the sinus, it is often challenging to insert a tool into the sinus at the proper location, and with the correct orientation. Moreover, external forces, such as those applied by the internal surface of the subject's nostril, may complicate the insertion.

Embodiments of the present invention address these challenges, by providing an insertion tube having a flexible distal portion that comprises a plurality of articulated sections. A ribbon, having a curved cross-section, runs through the lumen of the tube, and is connected to the distal portion at least at the distalmost one of the articulated sections. Prior to inserting the tube through the subject's nostril, and/or while the tube is inside the subject, the physician flexes the distal portion of the tube into the desired configuration, by pulling the ribbon. Subsequently, the tool may be passed through the tube.

Although the present description relates mainly to sinus procedures, it is noted that apparatus and methods described herein may be used to facilitate the insertion of any suitable type of tool into any suitable interior portion of a body of a subject, such as a stomach or a joint.

Apparatus Description

Figure 1:
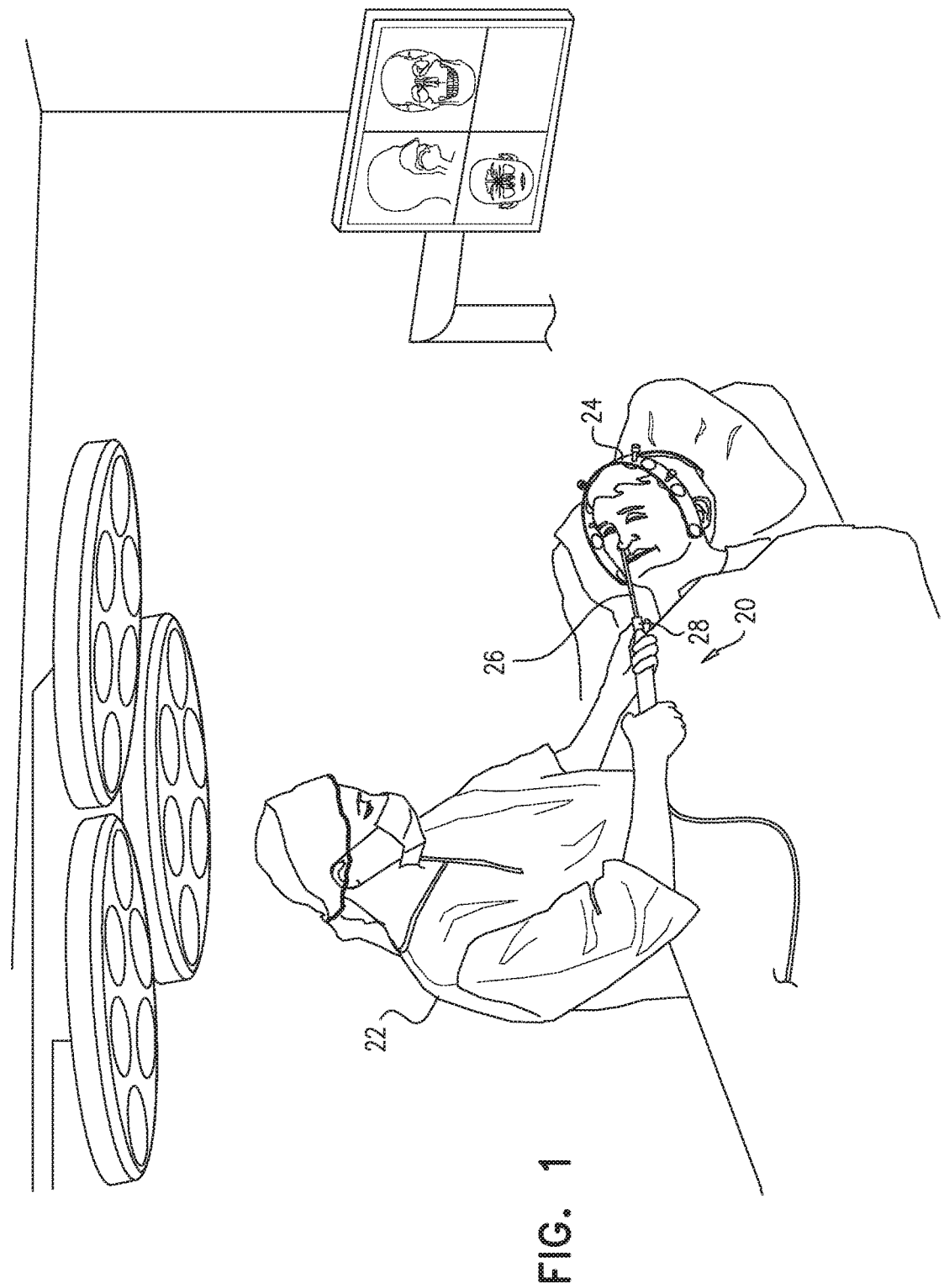

Reference is initially made to FIG. 1, which is a schematic illustration of apparatus 20 for facilitating insertion of a tool into a sinus of a subject 24, in accordance with some embodiments of the present invention.

Apparatus 20 comprises a tube 26, which typically has a cylindrical shape. A physician 22 inserts tube 26 into the sinus of subject 24 through a nostril of the subject. As further described below, using a control handle, comprising, for example, an adjustment dial 28, at the proximal end of the tube, physician 22 may flex and/or otherwise adjust the configuration of the distal portion of the tube, prior to inserting the tube, and/or while the tube is inside the subject. A medical instrument, such as a catheter that carries a balloon or camera, may then be inserted into the sinus through tube 26.

In some embodiments, the tube is equipped with sensors (not shown), such as electromagnetic sensors, which are used to track the position of the tube during the procedure.

Figure 2B:
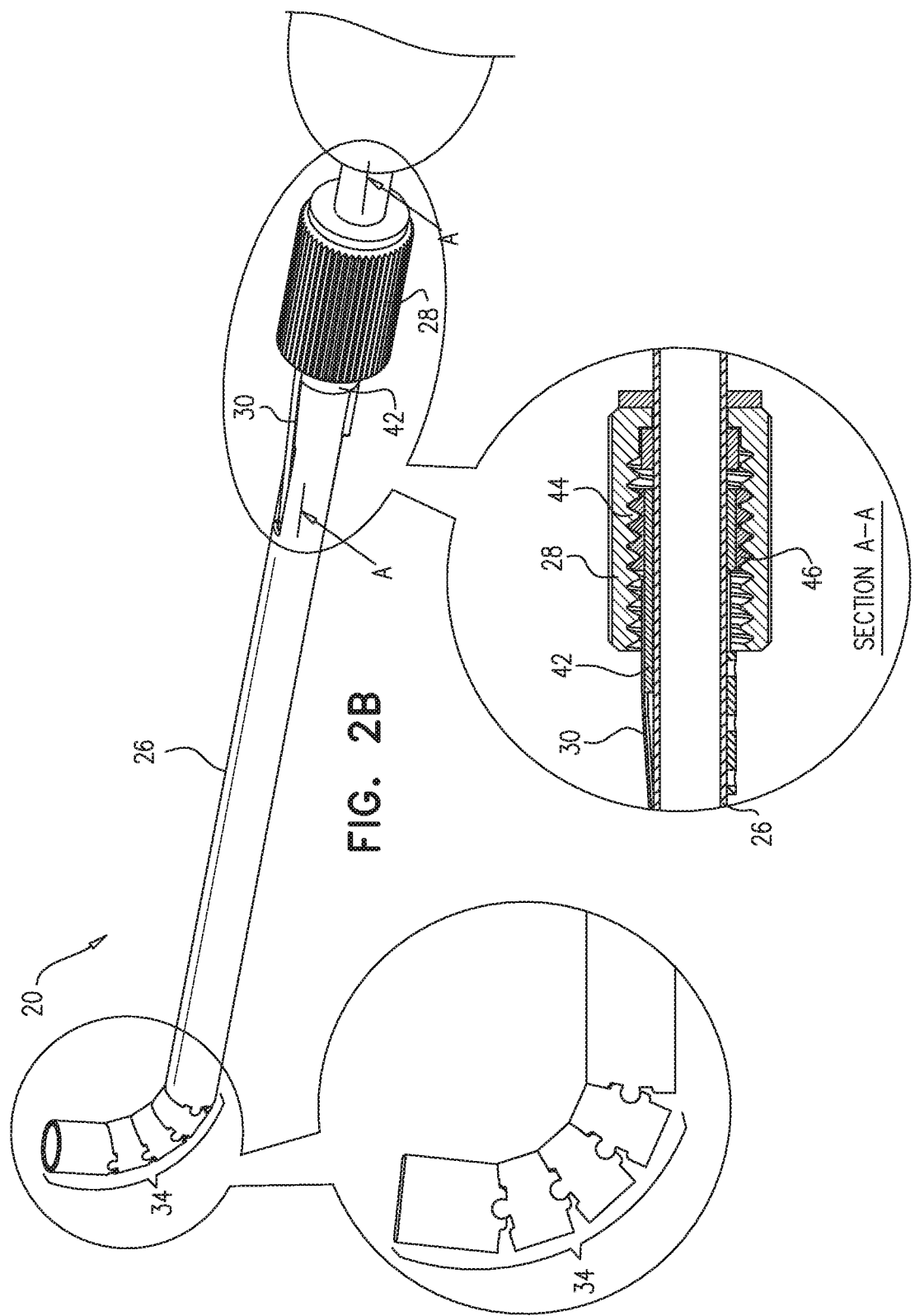

Reference is now made to FIGS. 2A-B, which are schematic illustrations of apparatus 20, in accordance with some embodiments of the present invention.

As shown in FIG. 2A, the distal portion of tube 26 is not contiguous, but rather, comprises a plurality of articulated sections 34. By moving with respect to each other, articulated sections 34 facilitate adjusting the configuration of the distal portion of the tube. For example, as shown in the figure, each of the articulated sections, with the exception of the distalmost section 38, may comprise protrusions 36, which swivelingly fit within complementary grooves formed in an adjacent section, such that the articulated sections may swivel with respect to each another. Thus, for example, in FIG. 2A, articulated section 34a comprises two protrusions 36 that swivelingly fit within two complementary grooves in the adjacent articulated section 34b, one such protrusion being shown in the figure, and the other protrusion being opposite the shown protrusion, on the far side of articulated section 34a.

In some embodiments, the protrusions protrude proximally, rather than distally. Thus, for example, distalmost section 38 may comprise protrusions that swivelingly fit within complementary grooves in articulated section 34b, rather than the reverse configuration that is shown in the figure.

In general, apparatus 20 may comprise any suitable number of articulated sections 34, e.g., between 3 and 10 articulated sections.

As shown in the inset transverse cross-section of tube 26, the tube is shaped to define a tube lumen 40. A ribbon 30, typically comprising nitinol, passes proximally-distally through tube lumen 40, and is connected to distalmost articulated section 38 (but not to the other articulated sections). As described immediately hereinbelow, ribbon 30 facilitates adjusting the configuration of the distal portion of the tube.

As shown in FIG. 2A, in the unflexed state of the tube, each of the articulated sections is generally flush with its neighbors along the portion of the circumference of the tube that is between the protrusions and opposite the ribbon, but is spaced apart from its neighbors along the portion of the circumference that is between the protrusions and occupied by the ribbon. Thus, as the ribbon is proximally pulled, each articulated section swivels toward its proximal neighbor, such that the open space that separates the articulated section from its proximal neighbor is closed. The distal portion of the tube is thus flexed (or "curved"), as shown in FIG. 2B. Conversely, by pushing the ribbon, the distal portion of the tube may be released into the unflexed state shown in FIG. 2A.

Typically, articulated sections 34 are covered by casing elements 32, which hold the articulated sections together, and prevent lateral flexing of the distal end of the tube. (For clarity, FIG. 2A shows only the proximalmost casing element 32, with the remainder of the casing elements being stripped from the articulated sections. Similarly, for clarity, FIG. 2B does not show any casing elements.)

The tube is sized and shaped for being comfortably inserted into the subject, and for allowing a medical instrument to be subsequently inserted through the tube lumen.

A control handle at the proximal end of the tube controls the ribbon. In some embodiments, as shown in FIG. 2A, the control handle comprises a turnable dial 28. By turning dial 28 in one direction, the ribbon is pulled, thus causing flexion of the distal portion of the tube. Conversely, by turning dial 28 in the opposite direction, the ribbon is pushed, thus causing the distal portion of the tube to be unflexed. For example, the proximal end of the ribbon may be coupled to a sliding element 42, which is configured to slide between an extreme proximal position and an extreme distal position. By turning the dial, sliding element 42 is slid proximally or distally, thus causing the distal end of the tube to be flexed or unflexed. For example, as shown in the inset longitudinal cross-section of the dial in FIG. 2A, the inner surface of the dial may be shaped to define (female) threading 44, which, by threadedly engaging complementary (male) threading 46 on sliding element 42, controls the position of the sliding element.

Typically, ribbon 30 has a curved cross-section. For example, the angle theta (θ) between two hypothetical lines that are tangent to respective ends of the cross-section of the ribbon may be between 50 and 70 degrees. The curved cross-section helps the ribbon resist buckling, when the ribbon is pushed. In some embodiments, ribbon 30 is at the distal end of a control tube, which runs, longitudinally, within tube lumen 40 from the control handle to the proximalmost articulated section. (Ribbon 30 thus runs within tube lumen 40 only at the flexible, distal portion of tube 26.) For example, ribbon 30 and the control tube may be formed together, as an integrated whole, by cutting away the majority of the circumference of a tube at the distal end of the tube. The ribbon is then pulled by pulling the tube, and pushed by pushing the tube. Since a tube is generally more resistant to buckling than a ribbon, such embodiments provide further resistance to buckling.

Alternatively or additionally, to help prevent buckling of the ribbon, the inside wall of the tube may be shaped to define protrusions that hold the ribbon against the inside wall of the tube, thus defining a "track" along which the ribbon slides.

FIG. 2B illustrates the tube in a flexed position. (The inset longitudinal cross-section of the dial in FIG. 2B shows sliding element 42—and hence, the proximal end of ribbon 30—at a more proximal position, relative to FIG. 2A, due to the dial having been turned.)

Typically, the turnable dial is further configured to, subsequently to turning, hold the ribbon in place, thus maintaining the configuration of the tube. For example, the engagement of threading 44 with threading 46, as shown in FIG. 2B, may prevent the sliding element from sliding unless the dial is once again turned.

Notwithstanding the particular embodiment illustrated in the figures, it is noted that any other suitable type of control handle—whether including a turnable dial, or not including a turnable dial—is incorporated within the scope of the present invention.

Subsequently to changing the configuration of the distal portion of the tube to the desired configuration, while the tube is inside the subject, a tool is passed longitudinally (distally) through lumen 40 and into the subject.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. A method, comprising:
    (a) by pulling a ribbon, flexing a distal portion of a tube, wherein a proximal portion of the tube defines a longitudinal axis, wherein pulling the ribbon comprises rotating a rotary actuator in a first angular direction about the longitudinal axis, wherein the ribbon is positioned to traverse an exterior wall of the tube distal to the rotary actuator, wherein the rotary actuator remains in a fixed position on the longitudinal axis upon rotating the rotary actuator in the first angular direction; and
    (b) subsequently, while the distal portion of the tube is flexed, passing a tool longitudinally through a lumen of the tube and into an interior portion of a body of a subject.

2. The method according to claim 1, wherein the interior portion of the body of the subject includes a sinus of the subject.

3. The method according to claim 1, wherein the rotary actuator comprises a dial.

4. The method according to claim 1, wherein the distal portion of the tube includes a plurality of articulated sections, the ribbon being coupled to a distalmost one of the articulated sections.

5. The method according to claim 4, wherein flexing the distal portion of the tube comprises flexing the distal portion of the tube by causing at least one of the articulated sections to swivel with respect to another one of the articulated sections.

6. The method according to claim 4, wherein at least one pair of the articulated sections includes: a first articulated section, shaped to define two grooves; and a second articulated section, comprising two protrusions configured to swivelingly fit within the grooves such that one of the first articulated section and the second articulated section swivels with respect to the other one of the first articulated section and the second articulated section, as the ribbon is pulled.

7. The method according to claim 1, wherein the ribbon has a curved cross-section.

8. The method according to claim 1, wherein the ribbon is at a distal end of a control tube that runs longitudinally within the tube lumen proximally to the distal portion of the tube, and wherein pulling the ribbon comprises pulling the ribbon by pulling the control tube.

9. The method according to claim 4, wherein the articulated sections are configured such that:
    (i) a first circumferential region of each articulated section defines a gap with the corresponding first circumferential region of each adjacent articulated section when the distal portion of the tube is in a straight configuration, and
    (ii) the first circumferential region of each articulation section is flush with the corresponding first circumferential region of each adjacent articulated section when the distal portion of the tube is in a flexed configuration.

10. The method according to claim 9, wherein the gap is V-shaped.

11. The method according to claim 4, wherein the articulated sections are configured such that:
    (i) a first circumferential region of each articulated section is flush with the corresponding first circumferential region of each adjacent articulated section when the distal portion of the tube is in a straight configuration, and
    (ii) the first circumferential region of each articulation section defines a gap with the corresponding first circumferential region of each adjacent articulated section when the distal portion of the tube is in a flexed configuration.

12. The method according to claim 11, wherein the articulated sections are further configured such that:
    (i) a second circumferential region of each articulated section defines a gap with the corresponding second circumferential region of each adjacent articulated section when the distal portion of the tube is in a straight configuration, and
    (ii) the second circumferential region of each articulation section is flush with the corresponding second circumferential region of each adjacent articulated section when the distal portion of the tube is in a flexed configuration.

13. The method according to claim 1, wherein the tool comprises a camera.

14. The method according to claim 1, wherein the tool comprises a balloon catheter.

15. The method according to claim 1, wherein the tool comprises a guidewire.

16. A method, comprising:
    (a) rotating a rotary actuator about a longitudinal axis defined by a proximal portion of a tube, wherein rotating the rotary actuator drives a linear actuator longitudinally relative to the tube and the rotary actuator, wherein the rotary actuator drives the linear actuator longitudinally along an exterior portion of the tube distal to the rotary actuator, wherein the linear movement of the linear actuator causes a distal portion of the tube to flex laterally away from the longitudinal axis;

(b) inserting the distal portion of the tube into a nasal cavity of a patient; and (c) advancing a tool through a lumen of the tube to thereby position a distal portion of the tool in the nasal cavity of the patient, wherein at least a portion of the advanced tool is disposed in the flexed distal portion of the tube.

17. The method according to claim 16, wherein the linear actuator comprises a ribbon.

18. The method according to claim 16, wherein advancing the tool comprises positioning the distal portion of the tool in a paranasal sinus of the patient.

19. The method according to claim 16, wherein rotating a rotary actuator is performed before inserting the distal portion of the tube into the nasal cavity of the patient.

20. A method, comprising:

(a) rotating a rotary actuator about a longitudinal axis defined by a proximal portion of a tube, wherein rotating the rotary actuator drives a linear actuator along the longitudinal axis in a distal direction relative to the rotary actuator, wherein the linear actuator transitions from an exterior position of the tube to an interior position of the tube through an opening defined by the tube, wherein the opening is located distal to the rotary actuator, wherein the linear movement of the linear actuator causes a distal portion of the tube to flex laterally away from the longitudinal axis;

(b) after rotating the rotary actuator, inserting the distal portion of the tube into a nasal cavity of a patient while the distal portion is in a flexed state; and (c) advancing a guidewire or balloon catheter through a lumen of the tube to thereby position a distal portion of the guidewire or balloon catheter in the nasal cavity of the patient, wherein at least a portion of the advanced guidewire or balloon catheter is disposed in the flexed distal portion of the tube.

\* \* \* \* \*